United States Patent [19]
Miyano et al.

[11] Patent Number: 5,849,961
[45] Date of Patent: Dec. 15, 1998

[54] OPTICALLY ACTIVE 1,1'-BIPHENANTHRYL-2,2'-DIOL, PROCESS FOR PREPARING THE SAME, AND RESOLVING REAGENT COMPRISING THE SAME

[75] Inventors: Sotaro Miyano, Sendai; Kenta Sakurai, Shiogama; Nobuyuki Koike; Tetsutaro Hattori, both of Sendai, all of Japan

[73] Assignee: Takasago International Corporation, Tokyo, Japan

[21] Appl. No.: 812,543

[22] Filed: Mar. 7, 1997

[30] Foreign Application Priority Data

Mar. 9, 1996 [JP] Japan .................................. 8-081017

[51] Int. Cl.$^6$ .................................................. C07C 35/42
[52] U.S. Cl. ............................................................. 568/714
[58] Field of Search ............................................. 568/714

[56] References Cited

FOREIGN PATENT DOCUMENTS 0647647A 4/1995 European Pat. Off. .

OTHER PUBLICATIONS

*The Journal of the American Chemical Society*, Nov. 3, 1993, vol. 115, No. 22, pp. 10372/10373, Hiroaki Sasai et al, "Catalytic Asymmetric Nitroaldol Reaction Using Optically Active Rare Earth BINOL Complexes: Investigation of the Catalyst.".

*The Journal of the Organic Chemistry*, Nov. 18, 1994, vol. 59, No. 23, Dongwei Cai et al, "Synthesis of Chiral 2,2'-Bis-(diphenylphosphino)-1,1'-binaphthyl )BINAP) via a Novel Nickel–Catalyzed Phosphine Insertion.".

Yamamura, K. et al, 'Chiral Liquid Crystal Mesogens. Synthesis and Determination of Absolute Configuration of Mesogens With 4,4'–Biphenanthryl Cores' Synlett. 1989, 1, pp. 18–19, abstract only.

*Primary Examiner*—C. Warren Ivy
*Assistant Examiner*—Garth M. Dahlen
*Attorney, Agent, or Firm*—Sughrue, Mion, Zinn, Macpeak & Seas, PLLC

[57] ABSTRACT

The novel optically active 1,1'-biphenanthryl-2,2'-diol is disclosed, which is obtained by preparing N((S)-1-phenylethyl)-1,1'-biphenanthryl-2,2'-diylthiophosphorylamide by using optically active phenylethylamine, recrystallizing the compound into an optically active compound, followed by reduction with a reducing agent. The diol compound according to the present invention is useful as a resolving reagent, a starting material of an optically active phosphine compound or a ligand in asymmetric synthesis, forming a complex with a transition metal or a rare earth element to provide a useful catalyst.

5 Claims, 1 Drawing Sheet

¹H NMR (600 MHz; ACETONE-d6)
7.08 (d, J = 9.07, H$_{10}$)
7.46 (d, J = 9.07, H$_3$)
7.49 (t, J = 7.44, H$_7$)
7.52 (d, J = 9.07, H$_9$)
7.62 (t, J = 7.64, H$_6$)
7.80 (dd, J = 7.79, 0.91, H$_8$)
8.06 (br, 2H)
8.75 (d, J = 8.33, H$_5$)
8.81 (d, J = 8.52, H$_4$)

¹³C NMR (600 MHz; ACETONE-d6)

OPTICALLY ACTIVE 1,1'-BIPHENANTHRYL-2,2'-DIOL, PROCESS FOR PREPARING THE SAME, AND RESOLVING REAGENT COMPRISING THE SAME

FIELD OF THE INVENTION

This invention relates to 1,1'-biphenanthryl-2,2'-diol, optically active 1,1'-biphenanthryl-2,2'-diol, a process for preparing the optically active 1,1'-biphenanthryl-2,2'-diol, and a resolving reagent comprising the optically active 1,1'-biphenanthryl-2,2'-diol. The novel optically active biphenanthryl derivative according to the present invention is useful as a resolving reagent, a starting material of an optically active phosphine compound or a ligand in asymmetric synthesis, forming a complex with a transition metal or a rare earth element to provide a useful catalyst.

BACKGROUND OF THE INVENTION

An optically active binaphthol is well known as a ligand or a starting material therefor in organic synthesis reactions, such as asymmetric hydrogenation, asymmetric isomerization, asymmetric hydrosilylation, asymmetric ene reaction, asymmetric hetero Diels-Alder reaction, asymmetric Michael reaction, and asymmetric nitroaldol reaction. A great number of reports have been made on the metal complex catalysts derived from the optically active binaphthol, such as The Chemical Society of Japan (ed.), *KAGAKU SOSETSU*, Vol. 32, pp. 237–238, "YUKI KINZOKU SAKUTAI KAGAKU" (1982), Ryoji Noyori, *Asymmetric Catalysis in Organic Synthesis*, A Wiley-Interscience Publication, K. Mikami, M. Terada, S. Narisawa, and T. Nakai, *SYNLETT*, pp. 255–265 (1992), M. Terada, S. Matsukawa, and K. Mikami, *J. Chem. Soc., Chem. Commun.*, pp. 327–328 (1993), M. Terada, K, Mikami, and T. Nakai, *Tetrahedron Letters*, Vol. 32, pp. 935–938 (1991), H. Sasai, T. Suzuki & M. Shibasaki, *J. Am. Chem. Soc.*, Vol. 114, pp. 4418–4420 (1992), H. Sasai, T. Suzuki & M. Shibasaki, *Tetrahedron Letters*, Vol. 34, pp. 851–854 (1993), H. Sasai, T. Suzuki & M. Shibasaki, *Tetrahedron Letters*, Vol. 35, pp. 6123–6126 (1994), H. Sasai, T. Suzuki & M. Shibasaki, *J. Am. Chem. Soc.*, Vol. 115, pp. 10372–10373 (1993), H. Sasai, T. Arai & M. Shibasaki, *J. Am. Chem. Soc.*, Vol. 116, pp. 1571–1572 (1994), JP-A-5-17491 (the term "JP-A" means an "unexamined published Japanese patent application"), and D. Cai, J. Payack, D. Bender, D. Hughes, T. Verhoeven & P. Reider, *J. Org. Chem.*, Vol. 59, pp. 7180–7181 (1994).

It has been reported that a binaphthol is an excellent optically active ligand in these asymmetric synthesis reactions and optically active phosphines derived from an optically active binaphthol exert similar effects.

*J. Am. Chem. Soc.*, Vol. 115, p. 10372 (1993) supra reports that an optically active nitroaldol compound is obtained from an aldehyde and nitromethane in the presence of a lanthanide-binaphthol complex prepared from an optically active binaphthol and a lanthanide metal.

*J. Am. Chem. Soc.*, Vol. 112, p. 3949 (1990) reports that the asymmetric ene reaction between an olefin and glyoxylic ester in the presence of an optically active binaphthol-titanium complex proceeds with a high asymmetric yield.

Further, *J. Org. Chem.*, Vol. 59, p. 7180 (1994) supra reports synthesis of optically active BINAP (2,2'-bis(diphenylphosphino)-1,1'-binaphthyl) from an optically active binaphthol.

However, these ligands and phosphine compounds are still wanting in chemical selectivity, catalytic activity, stereoselectivity, and the like in some asymmetric reactions or for some reaction substrates.

SUMMARY OF THE INVENTION

An object of the present invention is to provide a novel optically active ligand which is efficient and suited to the reaction substrate in optical resolution of various racemates or various asymmetric syntheses.

In order to solve the above problem, the inventors of the present invention have conducted an extensive study on optically active ligand compounds and found as a result that optically active 1,1'-biphenanthryl-2,2'-diol is excellent as a resolving reagent, an optically active ligand, and a starting material of an optically active phosphine compound. The present invention has been completed based on this finding.

The present invention relates to:

(1) 1,1'-biphenanthryl-2,2'-diol represented by formula (I):

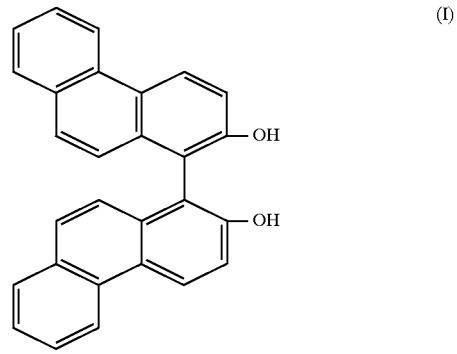

(2) optically active 1,1'-biphenanthryl-2,2'-diol represented by formula (II):

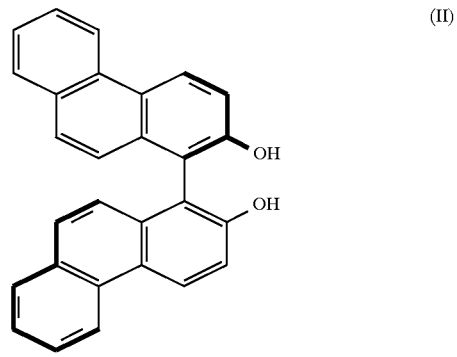

-continued

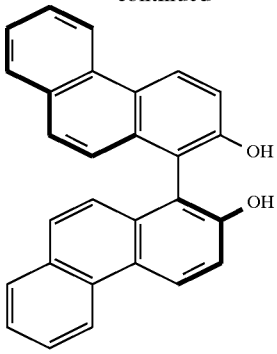

S.

(3) a process for preparing optically active 1,1'-biphenanthryl-2,2'-diol comprising preparing a complex from a copper salt and an amine, reacting 2-phenanthrol in the presence of the complex to form (±)-1,1'-biphenanthryl-2,2'-diol, reacting the (±)-1,1'-biphenanthryl- 2,2'-diol with thiophosphoryl chloride and optically active phenylethylamine in the presence of pyridine to form N-(1-phenylethyl)-1,1'-biphenanthryl-2,2'-diylthiophosphoramide, optically resolving the N-(1-phenylethyl)-1,1'-biphenanthryl-2,2'-diylthiophosphoramide by recrystallization, and hydrogenolyzing the resulting optically active compound, and (4) a resolving reagent comprising optically active 1,1'-biphenanthryl-2,2'-diol represented by formula (II):

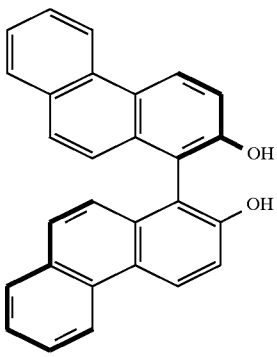

R.

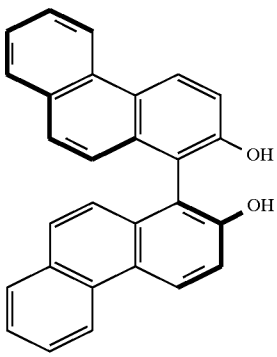

S.

DETAILED DESCRIPTION OF THE INVENTION

Figure 1:
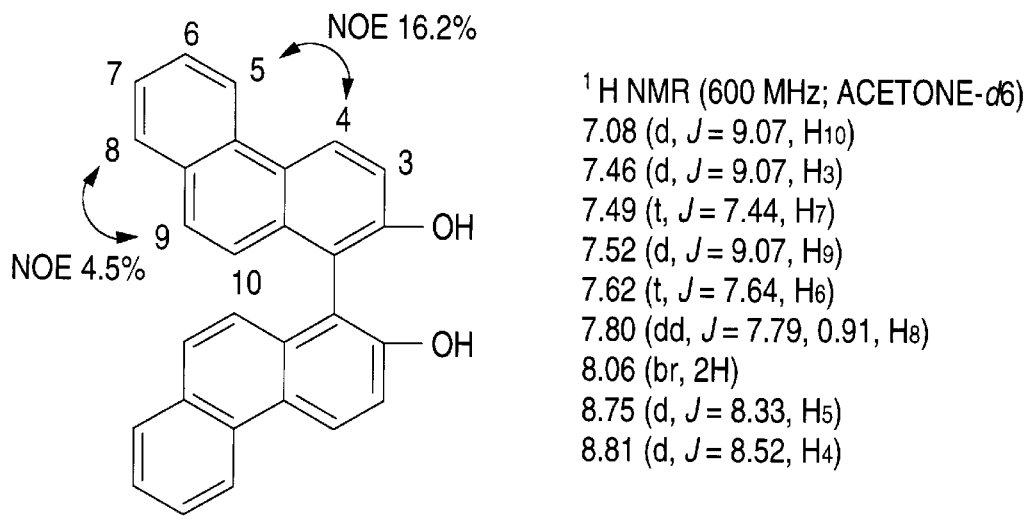
FIG. 1 shows the $^1$H-NMR spectral data of (±)-1,1'-biphenanthryl-2,2'-diol.

The present invention will further be described in detail.

The 1,1'-phenanthryl-2,2'-diol (I) according to the invention includes racemic modifications and optically active compounds.

The optically active (+)- or (−)-1,1'-biphenanthryl-2,2'-diol of the invention can be prepared, for example, as follows.

Phenanthrene is sulfonated with concentrated sulfuric acid and then treated with barium chloride to obtain barium 2-phenanthrenesulfonate. The resulting barium salt is subjected to alkali fusion in an electric oven and then treated with hydrochloric acid to obtain 2-phenanthrol. 2-Phenanthrol is subjected to oxidative coupling in the presence of a copper-amine complex to synthesize racemic 1,1'-biphenanthryl-2,2'-diol (I). The resulting diol is reacted with optically active phenylethylamine and thiophosphoryl chloride to afford (±)-N((S)-1-phenylethyl)-1,1'-biphenanthryl-2,2'-diylthiophosphorylamide. Recrystallization of the racemate gives an optically active compound, which is then hydrogenolyzed with a reducing agent, such as lithium aluminum hydride, to give optically active 1,1'-biphenanthryl-2,2'-diol with an optical purity reaching nearly 100%.

In the above process, when (+)-phenylethylamine is used, (+)-1,1'-biphenanthryl-2,2'-diol is obtained. When (−)-phenylethylamine is used, (−)-1,1'-biphenanthryl-2,2'-diol is obtained.

The step of oxidative coupling in the presence of a copper-amine complex is usually carried out by adding a methanolic or ethanolic solution of 2-phenanthrol with stirring to a copper-amine complex previously prepared by reacting a copper salt with 2 to 6 mols, preferably 3 to 4 mols, of an amine per mole of the copper salt in a solvent, e.g., methanol or ethanol. Useful copper salts include copper nitrate, cupric chloride, cupric acetate, and cupric nitrate, and hydrates of these salts. Useful amines include those described in Tetrahedron, Vol. 41, p. 3313 (1985), such as phenylethylamine, benzylamine, ethylamine, and naphthylamine. The copper-amine complex is usually used in an amount of 1 to 3 mols, preferably 1.0 to 1.1 mol, per mole of the substrate, i.e., phenanthrol. The solvent to be used for the oxidative coupling reaction includes methanol, ethanol, propanol, isopropyl alcohol, butanol, methylene chloride, and dichloroethane.

The step of converting the resulting diol to (±)-N((S)-1-phenylethyl)-1,1'-biphenanthryl-2,2'-diylthiophosphorylamide (hereinafter referred to compound A) is usually carried out in the co-presence of a base and a solvent at a temperature of 20° to 120° C. Suitable solvents include pyridine, methylene chloride, tetrahydrofuran, toluene, and benzene. Suitable bases include pyridine, triethylamine, and diisopropylamine. The base is used in an amount of 2 to 10 equivalents to the substrate, i.e., 1,1'-biphenanthryl-2,2'-diol (I). Pyridine is used to advantage, serving as both a solvent and a base.

The step of optically resolving compound A can be conducted by dissolving 1 part by weight of compound A in 1 part by volume (1 ml per gram of the substrate) of a solvent and adding thereto 3 to 5 parts by volume of an alcohol per part by weight of compound A thereby to precipitate a desired optically active compound. Suitable solvents to be used here include methyl acetate, ethyl acetate, and butyl acetate, and suitable alcohols to be used here include methanol, ethanol, and isopropyl alcohol. Alternatively, the step can be carried out by dissolving 1 part by weight of compound A in 1 to 3 parts by volume of a solvent under heating, followed by allowing the system to cool to precipitate a desired optically active compound.

The novel optically active 1,1'-biphenanthryl-2,2'-diol of the invention can be obtained by preparing N((S)-1-phenylethyl)-1,1'-biphenanthryl-2,2'-diylthiophosphorylamide by using optically active phenylethylamine, recrystallizing the compound into an optically active compound, followed by reduction with a reducing agent. This novel compound can be converted to an optically active phosphine compound, which can provides a transition metal complex useful as an asymmetric catalyst. Further, the optically active compound is a useful compound, which can be converted to a diastereomer by esterification with, e.g., 1,1'-binaphthyl-2,2'-dicarboxylic acid, the diastereomer can be optically resolved by recrystallization to give an optically active compound, which is then subjected to hydrogenolysis to obtain an optically active diol.

EXAMPLES

The invention will now be illustrated in greater detail with reference to Examples, but it should be understood that the invention is not deemed to be limited thereto. Unless otherwise indicated, all the percents are given by weight.

Measurements of various physical properties of reaction products obtained in Examples were made with the following equipment:

- $^1$H-NMR: JMN-GX400 (manufactured by Nihon Denshi K.K.)
- $^{31}$P-NMR: WEX-270 (manufactured by Nihon Denshi K.K.)
- GLC (Gas chromatography): GC-15A (manufactured by Shimadzu Corp.)
- HPLC (High performance liquid chromatography): LC-4A (manufactured by Shimadzu Corp.)

EXAMPLE 1

Synthesis of (−)-1,1'-Biphenanthryl-2,2'-diol ((−)-4)

(−)-1,1'-Biphenanthryl-2,2'-diol ((−)-4) was synthesized in accordance with the reaction scheme shown below:

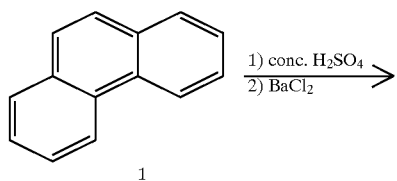

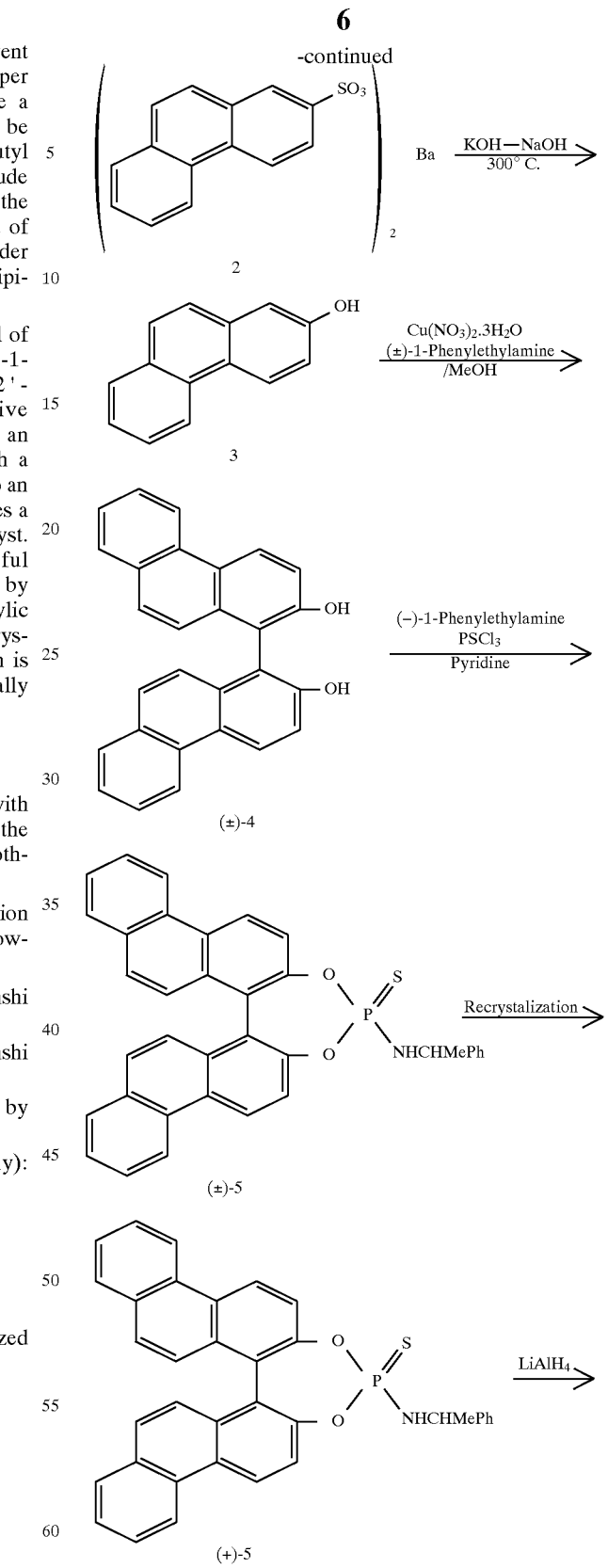

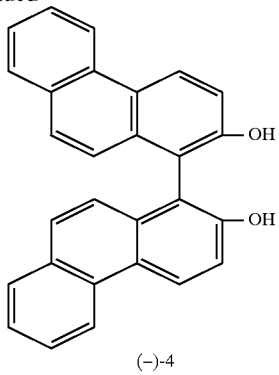

(−)-4

1) Synthesis of Barium 2-Phenanthrenesulfonate

In a 300 ml three-necked flask equipped with a dropping funnel, a mechanical stirrer, and a thermometer was put 50.0 g (0.284 mol) of phenanthrene (1) and melted at a bath temperature of 110° C. To the molten compound was added dropwise 40.0 ml of concentrated sulfuric acid over about 20 minutes while stirring taking care that the temperature of the reaction mixture might not exceed 120° C. After the addition, the reaction was continued for an additional 3 hour period. The reaction mixture was poured into 400 ml of water while hot, and immediately thereafter 100 ml of a 10N sodium hydroxide aqueous solution was added thereto, followed by cooling with ice. It was confirmed that the mixture was alkaline. The precipitate formed on cooling completely was collected by filtration and washed with a sodium chloride aqueous solution (90 g/l) to obtain a gray clayey solid. The solid was suspended in 750 ml of boiling water containing 10 ml of concentrated hydrochloric acid. The suspension was stirred for 20 minutes and filtered while hot. The filtrate was made neutral with sodium hydroxide granules and boiled by heating, and 10.0 g of barium chloride was added thereto, followed by allowing to cool. After allowing the system to stand overnight, the precipitated solid was collected by filtration and dried to give 210.1 g of a barium salt (2) as a gray solid.

2) Synthesis of 2-Phenanthrol

In a 50 ml nickel crucible were put 50.0 g of potassium hydroxide and 50.0 g of sodium hydroxide and fused in an electric oven at 300° C. To the molten caustic alkali was added 4.92 g (7.55 mmol) of barium 2-phenanthrenesulfonate (2), and 20.0 g each of potassium hydroxide and sodium hydroxide were added thereto, followed by further heating at 300° C. for 6 hours. The mixture was poured into 800 ml of water while hot and rendered acidic with concentrated hydrochloric acid. Phenanthrol thus released was extracted with four 500 ml portions of ethyl acetate and dried over anhydrous sodium sulfate. The solvent was removed by evaporation, and the resultant crude product was purified by silica gel column chromatography (n-hexane/ethyl acetate=3). Recrystallization from benzene yielded 1.51 g (5.7%) of 2-phenanthrol (3) as white crystals.

Melting point=165°–167° C.

3) Synthesis of (±)-1,1'-Biphenanthryl-2,2'-diol ((±)-4)

In a 300 ml two-necked flask having been purged with nitrogen was placed 2.10 g (17.3 mmol) of copper nitrate, and 30.0 ml of methanol was added thereto to dissolve copper nitrate. To the solution was added 3.12 g (25.7 mmol) of (±)-1-phenylethylamine to prepare a complex. A solution of 1.50 g (7.72 mmol) of 2-phenanthrol (3) in 20.0 ml of methanol was added thereto dropwise while stirring. After 24 hours, a solution prepared from 2.08 g (8.6 mmol) of copper nitrate, 2.71 g (22.4 mmol) of (±)-1-phenylethylamine, and 20.0 ml of methanol was added, followed by stirring for 6 hours. To the reaction mixture was added 100 ml of 2N diluted hydrochloric acid, and methanol was removed by evaporation. The residue was extracted with four 50 ml portions of ethyl acetate. The organic layer was washed successively with two 100 ml portions of a 2N hydrochloric acid aqueous solution and three 100 ml portions of water, and dried over magnesium sulfate. The solvent was evaporated off, and a brown solid residue (2.30 g) was purified by silica gel column chromatography (n-hexane/ethyl acetate=4) to give 1.08 g (72%) of (±)-1,1'-biphenanthryl-2,2'-diol as white crystals.

Melting point: 297.3°–298.6° C.

IR (KBr) cm$^{-1}$: 3456, 1593, 1459, 1352, 1234, 1168, 1145, 815, 749

$^1$H-NMR: see FIG. 1

Figure 2:
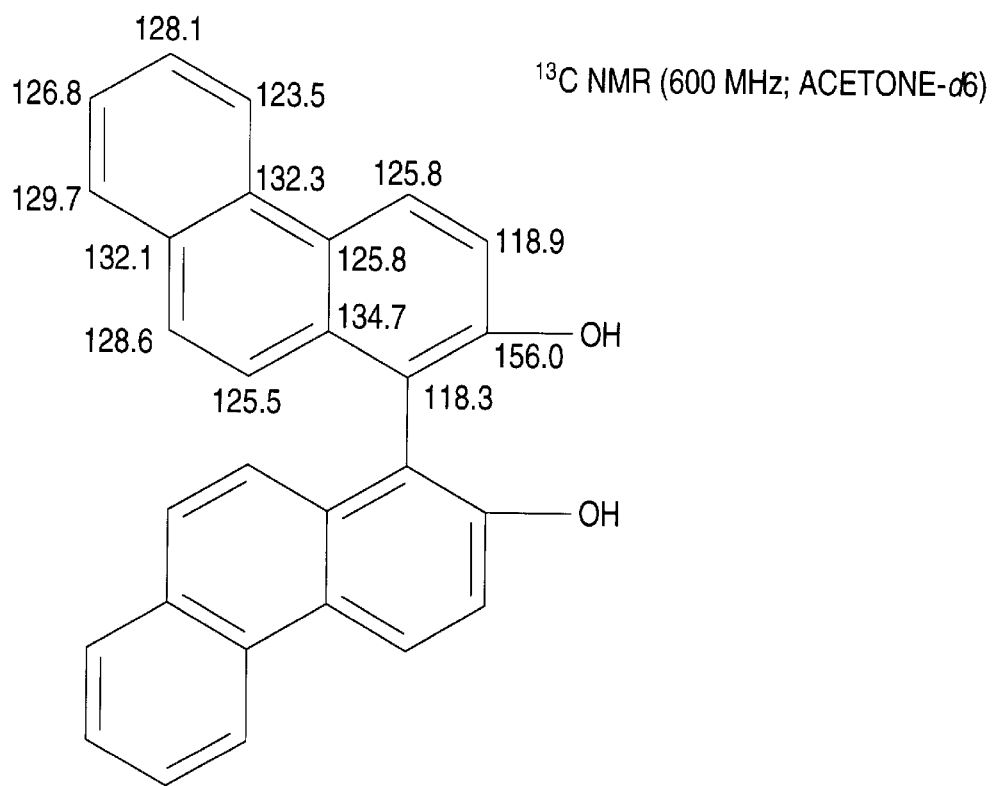
FIG. 2 shows the $^{13}$C-NMR spectral data of (±)-1,1'-biphenanthryl-2,2'-diol.

$^{13}$C-NMR: see FIG. 2

Elementary analysis for $C_{28}H_{18}O_2$: Calcd. (%): C 87.42; H 4.70 Found (%): C 87.14; H 4.66

4) Synthesis of (±)-N-((S)-1-Phenylethyl)-1,1'-biphenanthryl-2,2'-diylthiophosphoramide ((±)-5)

In a flask purged with nitrogen were put 400 mg (1.04 mmol) of the (±)-1,1'-biphenanthryl-2,2'-diol ((±)4) synthesized in (3) above, 8.0 ml of pyridine, and 0.115 ml (1.13 mmol) of thiophosphoryl chloride and cooled with ice. To the mixture was added 0.145 ml (1.12 mmol) of (S)-(−)-1-phenylethylamine, followed by heating under reflux for 4 hours. After allowing the mixture to cool, the reaction was stopped with 15 ml of 10% sulfuric acid. The reaction mixture was extracted with four 15.0 ml portions of dichloromethane, and the resulting organic layer was washed with two 15 ml portions of 10% sulfuric acid and dried over sodium sulfate. The solvent was removed by evaporation, and the residue (604 mg) was purified by silica gel column chromatography (n-hexane/ethyl acetate=5) to afford 410 mg (70%) of (±)-N-((S)-1-phenylethyl)-1,1'-biphenanthryl-2,2'-diylthiophosphoramide as white crystals.

$^1$H-NMR (CDCl$_3$) δ: 1.54 (d, J=6.75), 1.61 (d, J=6.77), 3.48–3.75 (m, 1H), 4.61–4.94 (m, 1H), 7.10–7.92 (m, 18H), 8.59–9.02 (m, 3H)

5) Optical Resolution [Preparation of (+)-N-((S)-1-Phenylethyl)-1,1'-biphenanthryl-2,2'-diylthiophosphoramide ((+)-5)]

In 0.4 ml of ethyl acetate was dissolved 400 mg of (±)-N-((S)-1-phenylethyl)-1,1'-biphenanthryl-2,2'-diylthiophosphoramide ((±)-5) while hot, and 1.6 ml of ethanol was slowly added thereto dropwise to precipitate crystals. After allowing to cool, the crystals were collected by filtration. The filtrate was concentrated, and the residue was recrystallized from acetonitrile. The combined crystals were suspended in acetonitrile and heated under reflux, followed by allowing to cool, and the crystals were collected by filtration to yield 154 mg (77%) of (+)-N-((S)-1-phenylethyl)-1,1'-biphenanthryl-2,2'-diylthiophosphoramide ((+)-5) as white crystals.

Melting point: 170°–171° C.

$[\alpha]_D^{25}$=+443.8° (c=0.64, CHCl$_3$)

IR (KBr) cm$^{-1}$: 3385, 1455, 1233, 984, 876, 844, 814, 747

$^1$H-NMR (CDCl$_3$) δ: 1.59 (d, J=6.76, 3H), 3.66 (t, J=9.44, 1H), 4.61–4.74 (m, 1H)

6) Preparation of (−)-1,1'-Biphenanthryl-2,2'-diol ((−)-4)

In a flask purged with nitrogen was put 30.1 mg (0.053 mmol) of (+)-N-((S)-1-phenylethyl)-1,1'-biphenanthryl-2, 2'-diylthiophosphoramide ((+)-5) and dissolved in 4.0 ml of tetrahydrofuran. To the solution was added 10.2 mg (0.266 mmol) of lithium aluminum hydride under ice-cooling, and the mixture was allowed to react at room temperature for 3 hours. The reaction was ceased by addition of 0.5 ml of ethyl acetate, and the reaction mixture was poured into 15 ml of 0.5N diluted hydrochloric acid and extracted with four 10 ml portions of ethyl acetate. The organic layer was washed successively with two 15 ml portions of 0.5N diluted hydrochloric acid and two 15 ml portions of water and dried over sodium sulfate. The solvent was removed by evaporation, and the residue (39.5 mg) was purified by thin layer chromatography (n-hexane/ethyl acetate=1) to give 19.2 mg (94%) of the title compound as white crystals.

Melting point: 244°–245° C.
$[\alpha]_D^{25}$=−34.0° (c=0.95; CHCl$_3$)
100% e.e. (measured with a Pirkle column; 30% isopropyl alcohol in n-hexane)

APPLICATION EXAMPLE 1

Production of (−)-1,1'-Binaphthyl-2,2'-dimethanol ((−)-8) by Optical Resolution (−)-1,1'-Binaphthyl-2,2'-dimethanol ((−)-8) was obtained by optical resolution in accordance with the following reaction scheme:

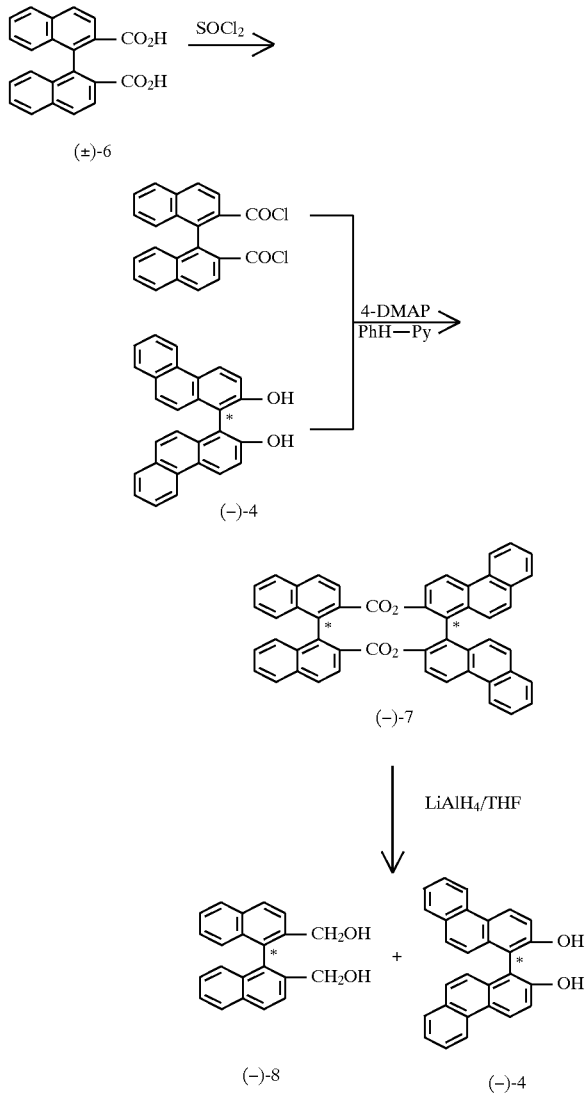

1) Preparation of Cyclic Diester [(−)-1,1'-Biphenanthryl-2,2'-yl 1,1'-Binaphthyl-2,2'-dicarboxylate ((−)-7)]

(Preparation of Acid Chloride)

In a flask equipped with a condenser were put 755 mg (2.20 mmol) of (±)-1,1'-binaphthyl-2,2'-dicarboxylic acid ((±)-6) and 10.0 ml of thionyl chloride, and the mixture was heated under reflux for 3 hours. Excess thionyl chloride was evaporated, and the residue was dried under reduced pressure for 2 hours.

(Esterification)

In a 500 ml three-necked flask equipped with two dropping funnels and a reflux condenser was put 538 mg (4.40 mmol) of 4-dimethylaminopyridine (DMAP). After displacing the atmosphere with nitrogen, DMAP was dissolved in 160 ml of dried benzene and 5.0 ml of dried pyridine. To the resulting solution were added dropwise a solution of 851 mg (2.20 mmol) of (−)-1,1'-biphenanthryl-2,2'-diol ((−)-4) in 70 ml of dried benzene and a solution of the above-prepared acid chloride in 70 ml of benzene at the same rate of addition over a period of 1 hour while heat-refluxing the system. After the addition, the reaction was further continued for an additional 2 hour period. The reaction was stopped with 150 ml of 2N diluted hydrochloric acid, and the reaction mixture was extracted with three 100 ml portions of ethyl ether. The organic layer was washed successively with 200 ml of 2N diluted hydrochloric acid and three 200 ml portions of water and dried over magnesium sulfate. The solvent was removed by evaporation, and the residual pale yellow solid was purified by silica gel column chromatography (n-hexane/methylene chloride=1) to afford 170 mg (11%) of (−)-1,1'-biphenanthryl-2,2'-yl 1,1'-binaphthyl-2,2'-dicarboxylate ((−)-7) as white crystals.

$[\alpha]_D^{25}$=−397° (c=0.51, CHCl$_3$)
IR (KBr) cm$^{-1}$: 1750, 1461, 1324, 1271, 1228, 1202, 1107, 1050, 820, 747
$^1$H-NMR (CDCl$_3$) δ: 6.93–7.95 (m, 24H), 8.62–8.75 (m, 4H)
Elementary Analysis for C$_{50}$H$_{28}$O$_4$: Calcd. (%): C 86.69; H 4.07 Found (%): C 86.79; H 4.32
FD-MS m/z: 694(8), 693(36), 693 (M$^+$; 100), 346 (M$^{2+}$; 2)

2) Production of (−)-1,1'-Binaphthyl-2,2'-dimethanol ((−)-8)

In a flask having been purged with nitrogen was put 62.4 mg (0.09 mmol) of (−)-1,1'-biphenanthryl-2,2'-yl 1,1'-binaphthyl-2,2'-dicarboxylate and dissolved in 10.0 ml of tetrahydrofuran. To the solution was added 82.6 mg (2.18 mmol) of lithium aluminum hydride while cooling with ice, and the mixture was allowed to react at room temperature for 6 hours, followed by cooling with ice. The reaction was stopped by addition of 2.0 ml of ethyl acetate. After a few drops of water were added, the reaction mixture was poured into 15 ml of 0.5N diluted hydrochloric acid and extracted with four 15 ml portions of ethyl acetate. The organic layer was washed with two 15 ml portions of water and dried over sodium sulfate. The solvent was removed by evaporation, and the residue (81.9 mg) was purified by thin layer chromatography (n-hexane/ethyl acetate=2).

(−)-1,1'-Binaphthyl-2,2'-dimethanol:
Yield: 25.6 mg (92%); white crystals
Optical purity: 98% e.e.
(+)-R-1,1'-Binaphthyl-2,2'-dimethanol (100% e.e.)
$^1$H-NMR (CDCl$_3$) δ: 3.47 (br, 2H), 4.07 (d, J=11.5 Hz, 2H), 4.35 (d, J=11.5 Hz, 2H), 7.00 (d, J=8.44 Hz, 2H), 7.21 (t, J=7.55 Hz, 2H), 7.44 (t, J=7.49 Hz, 2H), 7.66 (d, J=8.45 Hz, 2H), 7.90 (d, J=8.22 Hz, 2H), 7.93(d, J=8.46 Hz, 2H)
Recovered (−)-1,1'-biphenanthryl-2,2'-diol:
Yield: 31.1 mg (89%); white crystals
$[\alpha]_D^{24}$ =−32.0° (c=1.60; CHCl$_3$)

While the invention has been described in detail and with reference to specific embodiments thereof, it will be appar-

What is claimed is:

1. 1,1'-Biphenanthryl-2,2'-diol represented by formula (I):

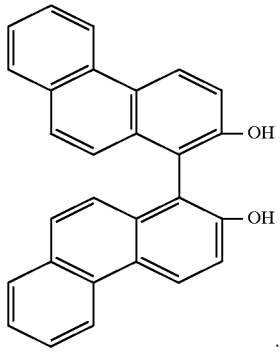
(I)

2. Optically active 1,1'-biphenanthryl-2,2'-diol represented by formula (II):

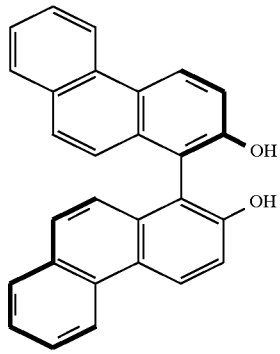
(II)

R.

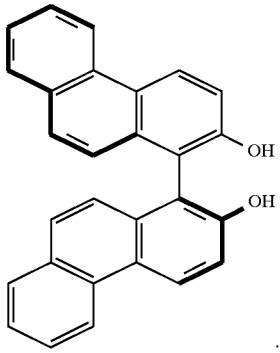

S.

3. A process for preparing optically active 1,1'-biphenanthryl-2,2'-diol comprising preparing a complex from a copper salt and an amine, reacting 2-phenanthrol in the presence of the complex to form (±)-1,1'-biphenanthryl-2,2'-diol, reacting the (±)-1,1'-biphenanthryl-2,2'-diol with thiophosphoryl chloride and optically active phenylethylamine in the presence of pyridine to form N-(1-phenylethyl)-1,1'-biphenanthryl-2,2'-diylthiophosphoramide, optically resolving the N-(1-phenylethyl)-1,1'-biphenanthryl-2,2'-diylthiophosphoramide by recrystallization, and hydrogenolyzing the resulting optically active compound.

4. The process as claimed in claim 3, wherein said copper salt is at least one selected from copper nitrate, cupric chloride, cupric acetate, or cupric nitrate and said amine is at least one selected from phenylethylamine, benzylamine, ethylamine, or naphthylamine.

5. In a method for resolving a compound using a resolving reagent, the improvement wherein the resolving reagent comprises optically active 1,1'-biphenanthryl-2,2'-diol represented by formula (II):

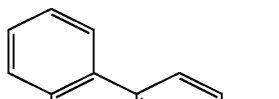
(II)

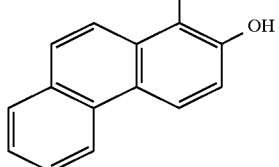

R.

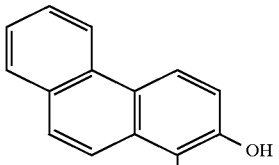

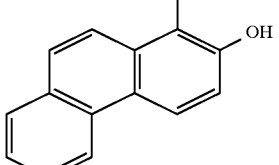

S.

* * * * *